United States Patent
Delnevo et al.

(10) Patent No.: US 7,316,662 B2
(45) Date of Patent: Jan. 8, 2008

(54) INFUSION DEVICE FOR MEDICAL USE

(75) Inventors: Annalisa Delnevo, Sant'Agata Bolognese (IT); Luca Caleffi, Mirandola (IT)

(73) Assignee: Gambro Lundia AB, Lund (SE)

( * ) Notice: Subject to any disclaimer, the term of this patent is extended or adjusted under 35 U.S.C. 154(b) by 342 days.

(21) Appl. No.: 10/520,529

(22) PCT Filed: Jun. 12, 2003

(86) PCT No.: PCT/IB03/02243

§ 371 (c)(1),
(2), (4) Date: Jan. 7, 2005

(87) PCT Pub. No.: WO2004/004807

PCT Pub. Date: Jan. 15, 2004

(65) Prior Publication Data

US 2006/0058774 A1    Mar. 16, 2006

(30) Foreign Application Priority Data

Jul. 9, 2002 (IT) .......................... MI2002A1497
Apr. 18, 2003 (IT) .......................... MO2003A0105

(51) Int. Cl.
*A61M 37/00* (2006.01)
*A61N 1/30* (2006.01)
*A61M 1/00* (2006.01)

(52) U.S. Cl. .................. 604/6.16; 604/27; 604/21; 604/30; 604/80

(58) Field of Classification Search ............... 604/4.01, 604/5.01, 6.09, 6.1, 6.11, 6.16, 80, 151, 246, 604/247, 262, 251, 254, 258, 65–67, 82, 604/126, 500, 21, 29, 30; 210/645; 422/44; 417/477.1, 477.11

See application file for complete search history.

(56) References Cited

U.S. PATENT DOCUMENTS

| | | |
|---|---|---|
| 3,570,484 A | 3/1971 | Steer |
| 3,601,152 A | 8/1971 | Kenworthy |
| 3,710,942 A | 1/1973 | Rosenberg |
| 3,804,113 A | 4/1974 | Garcea |
| 3,886,937 A | 6/1975 | Bobo et al. |

(Continued)

FOREIGN PATENT DOCUMENTS

| | | |
|---|---|---|
| DE | 31 00 442 C1 | 9/1982 |
| DE | 39 22 291 C1 | 11/1990 |
| EP | 0 240 590 B1 | 10/1987 |
| EP | 0 247 213 A1 | 12/1987 |
| EP | 0 247 824 B1 | 12/1987 |
| EP | 0 261 317 B1 | 3/1988 |
| EP | 0 452 045 B1 | 10/1991 |
| EP | 0 474 069 B1 | 3/1992 |
| EP | 0 477 973 A1 | 4/1992 |
| EP | 0 638 328 A1 | 2/1995 |

(Continued)

*Primary Examiner*—Leslie Deak
(74) *Attorney, Agent, or Firm*—Finnegan, Henderson, Farabow, Garrett & Dunner, L.L.P.

(57) ABSTRACT

An infusion device for medical use has a container designed to hold a specified quantity of a liquid to be infused into a patient, a weighing device associated for operation with the container to measure the weight of the container and emit a corresponding signal, a transport line connected to the container, a pump, and a control unit associated with the weighing device and with the pump. The control unit is capable of detecting the end of infusion condition and of commanding the pump to stop the transport of fluid. A separator for continuously separating fluid into a gaseous portion and a liquid portion operates in the infusion line downstream of the pump and prevents the infusion of gas during the stopping transient of the pump at the end of infusion.

31 Claims, 12 Drawing Sheets

U.S. PATENT DOCUMENTS

| | | | |
|---|---|---|---|
| 3,889,710 A | 6/1975 | Brost | |
| 3,978,857 A | 9/1976 | McPhee | |
| 3,990,439 A | 11/1976 | Klinger | |
| 4,005,710 A | 2/1977 | Zeddies et al. | |
| 4,031,891 A | 6/1977 | Jess | |
| 4,084,606 A | 4/1978 | Mittleman | |
| 4,141,379 A | 2/1979 | Manske | |
| 4,181,146 A | 1/1980 | Goglio | |
| 4,190,426 A | 2/1980 | Ruschke | |
| 4,222,407 A | 9/1980 | Ruschke et al. | |
| 4,246,932 A | 1/1981 | Raines | |
| 4,286,628 A | 9/1981 | Paradis et al. | |
| 4,310,017 A | 1/1982 | Raines | |
| 4,349,035 A | 9/1982 | Thomas et al. | |
| 4,354,492 A | 10/1982 | McPhee | |
| 4,369,812 A | 1/1983 | Paradis et al. | |
| 4,395,260 A | 7/1983 | Todd et al. | |
| 4,447,230 A | 5/1984 | Gula et al. | |
| 4,535,820 A | 8/1985 | Raines | |
| 4,556,086 A | 12/1985 | Raines | |
| 4,646,781 A | 3/1987 | McIntyre et al. | |
| 4,683,916 A | 8/1987 | Raines | |
| 4,687,473 A | 8/1987 | Raines | |
| 4,729,401 A | 3/1988 | Raines | |
| 4,819,684 A | 4/1989 | Zaugg et al. | |
| 5,025,829 A | 6/1991 | Edwards et al. | |
| 5,064,168 A | 11/1991 | Raines et al. | |
| 5,308,333 A | 5/1994 | Skakoon | |
| 5,322,518 A | 6/1994 | Schneider et al. | |
| 5,402,982 A | 4/1995 | Atkinson et al. | |
| 5,439,451 A | 8/1995 | Collinson et al. | |
| 5,447,417 A * | 9/1995 | Kuhl et al. | 417/477.11 |
| 5,578,223 A * | 11/1996 | Bene et al. | 210/85 |
| 5,605,540 A * | 2/1997 | Utterberg | 604/80 |
| 5,613,663 A | 3/1997 | Schmidt et al. | |
| 5,617,897 A | 4/1997 | Myers | |
| 5,623,969 A | 4/1997 | Raines | |
| 5,634,905 A | 6/1997 | Rudolph, Jr. | |
| 5,698,090 A | 12/1997 | Bene et al. | |
| 5,727,594 A | 3/1998 | Choksi | |
| 5,769,811 A * | 6/1998 | Stacey et al. | 604/4.01 |
| 5,771,935 A | 6/1998 | Myers | |
| 6,032,926 A | 3/2000 | Fuchs | |
| 6,106,727 A | 8/2000 | Krasnoff et al. | |
| 6,390,130 B1 | 5/2002 | Guala | |
| 6,409,707 B1 | 6/2002 | Guala | |

FOREIGN PATENT DOCUMENTS

| | | |
|---|---|---|
| EP | 0 784 988 A1 | 7/1997 |
| EP | 0 790 065 A2 | 8/1997 |
| EP | 0 848 964 A1 | 6/1998 |
| EP | 1 099 456 B1 | 2/2003 |
| EP | 1 099 457 B1 | 9/2003 |
| GB | 2 000 685 A | 1/1979 |

\* cited by examiner

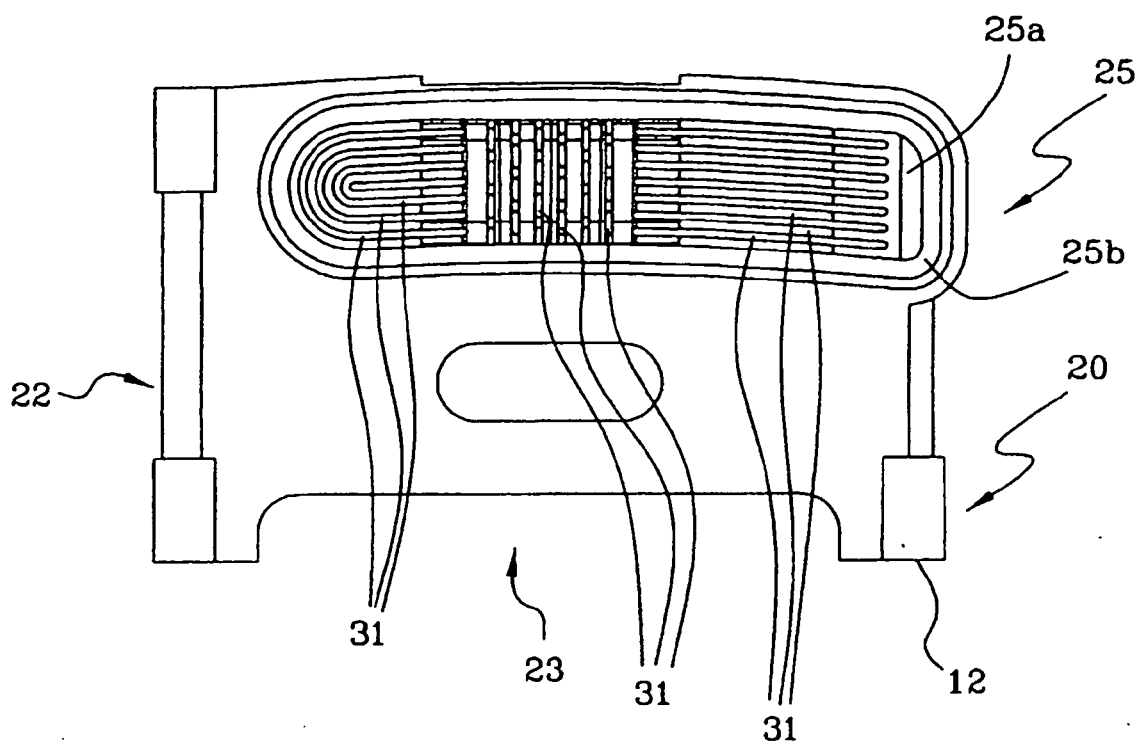

INFUSION DEVICE FOR MEDICAL USE

BACKGROUND OF THE INVENTION

The present invention relates to an infusion device for medical use.

In particular, the device of the invention is used in apparatus for the extracorporeal treatment of blood, for example apparatus for dialysis and/or plasmapheresis, in order to provide an infusion line which can be connected to an extracorporeal blood circuit associated with the aforementioned apparatus; the device in question can also be used for forming an infusion line which can be connected directly to the patient's vascular system.

As is known, a conventional infusion line comprises at least one length of tubing designed to connect a bag containing a specified infusion liquid to an extracorporeal blood circuit or directly to a patient through conventional access means such as needles, catheters or the like.

A pump, of the peristaltic type for example, can be provided on the infusion line for moving the infusion fluid in the desired way. For example, U.S. Pat. No. 5,698,090 in the name of Hospal Industrie describes an infusion line comprising a bag containing a replacement liquid, associated for operation with a balance designed to measure the weight of the bag and send a corresponding electrical signal to a control unit.

The control unit also acts on a peristaltic pump positioned on the infusion line; in particular, the unit controls the angular velocity of the pump in a suitable way according to the difference between the actual consumption signalled by the balance and the value set by the user.

Downstream of the peristaltic pump, the infusion line is connected to a collection chamber in which the infusion liquid can be combined with the blood obtained from a venous branch of an extracorporeal blood circuit.

Downstream of the aforesaid chamber, the blood, having been enriched with the infusion liquid, is returned to the patient's cardiovascular system.

The device described above can be used to control the actual flow and consequently the velocity of the infusion pump, and to achieve a separation of liquid and air such that the propagation of dangerous gas particles towards the patient is prevented.

Because of the presence of the balance and the control unit, if the total contents of liquid in the bag are known, the pump can be stopped and the suction of air bubbles from the bag prevented when the condition is reached in which the liquid in the bag has been used up.

However, it should be noted that there is an intrinsic minimum time interval between the actual emptying of the bag and the detection of this situation by the system consisting of the balance combined with the control unit. Consequently, in order to ensure the reliable operation of the described system, it is necessary to have a collection chamber (often referred to as a "bubble trap") in the infusion line, in which a specified volume of liquid can be held constantly; in normal operating conditions, the collection chamber holds this specified volume of fluid and enables the control system and balance to have sufficient time to detect when the end of infusion condition has actually been reached.

It should be noted that the detection of an end of infusion condition at the correct time is also important for the purpose of avoiding a discrepancy between the prescribed amount of infusion liquid for the patient and the actual infusion provided by the machine.

In addition to the solution described above, in which a balance is used to detect the end of infusion condition, widespread use has also been made in the past of solutions using level sensors, of the optical and/or ultrasonic type for example, which can interact with an infusion liquid collecting chamber, typically located in an intermediate area of the infusion line.

In the presence of a specified flow of liquid from the bag, the infusion liquid collecting chamber forms a liquid level and a reservoir for separating any air bubbles.

A level sensor associated with the chamber can be used to check and detect any fall in the level, permitting immediate recognition of a danger condition caused by the end of the supply of infusion liquid.

Clearly, if they are to operate correctly, the level sensors described above for detecting any fall in level or the presence of air bubbles in the flow directed towards the patient also require the presence of a collection chamber in the infusion line, for the formation of a level which will be detectable.

In other words, according to the known technical solutions, in order to enable an end of infusion condition to be detected and to ensure the reliable separation of air from the fluid directed towards the patient, it is necessary to provide a proper collection chamber or drip chamber in the infusion line, where the infusion fluid can accumulate, thus considerably reducing its velocity.

In practice, the collection chamber has a radial dimension considerably greater than that of the infusion tube, and, in the manufacturing process, is typically made separately from the rest of the line. The various lengths of tubing forming the infusion line and the collection chamber then undergo a rather complicated assembly process which considerably increases the total costs of the infusion line.

Furthermore, in the case of infusion lines interacting with level sensors, it is necessary to use optical or acoustic detectors which further increase the weight of the structure of the device. The control system has to be programmed to coordinate and control the signals received from the sensors.

Finally, all the known devices require the presence, downstream of the pump, of at least one safety valve, for example a clamp, which can close the tubing as soon as the condition of the end of infusion or the approaching end of infusion is detected.

Clearly, the fluid collection chamber can separate air from the liquid only when a minimum quantity of liquid is present in the chamber: if the liquid in the collection chamber is used up (this inevitably occurs after a certain time when the infusion liquid has been used up, unless the infusion pump is stopped at the correct time), there will be a transfer of gas towards the patient.

Finally, it should also be mentioned that there are known air-liquid separators of the type comprising a containing body forming two adjacent chambers separated by a hydrophilic membrane; the containing body has an inlet aperture for a fluid comprising liquid and gas particles. The liquid can pass through the hydrophilic membrane and emerge through an outlet aperture. The gas which reaches the first chamber is discharged through secondary apertures positioned upstream of the hydrophilic membrane, at least one hydrophobic membrane being used at these apertures to prevent the liquid from passing through.

The device which has been described allows the fluid, containing gas particles, to be separated into two parts, namely a liquid portion which emerges from the outlet aperture provided in the second chamber, and a gas portion which is released through the secondary apertures provided in the first chamber.

It should be noted that the air separator device which has been described does not require a constant presence of liquid stagnating within it in order to separate the gas; in other words, the fluid passing through the separation device is continuously divided into liquid, which continues along the line, and gas, which is discharged to the exterior.

SUMMARY OF THE INVENTION

In this situation, the object of the present invention is to provide a novel infusion device for the infusion of a liquid from a bag using a line having a very simple structure and overcoming all the drawbacks described above.

In particular, an object of the present invention is to provide an infusion device which does not require the use of a chamber for collecting the fluid upstream of the infusion point, and which does not require the presence of any optical or ultrasonic level sensor.

In particular, an object of the present invention is to combine efficiently, in an infusion line, the presence of a balance operating on the infusion bag with the presence of a special system capable of continuously preventing the passage of air to the patient during the detection of the end of infusion condition, in such a way as to make the whole infusion line extremely simple, efficient and reliable, so that there is theoretically no need to have further safety systems (clamps or other devices) for stopping the flow along the line.

Finally, an object of the present invention is to provide an infusion line which allows a plurality of bags to be incorporated, with a simple means of changing from one bag to the next when the liquid contained in each infusion bag is used up.

These and other objects, which will be made clearer in the following description, are essentially achieved by an infusion device according to the descriptions in one or more of the attached claims.

Further characteristics and advantages will be made clearer by the detailed description of a preferred, but not exclusive, embodiment of an infusion device according to the present invention.

BRIEF DESCRIPTION OF THE DRAWINGS

This description is provided below with reference to the attached drawings, provided solely for guidance and therefore without restrictive intent, in which:

FIG. 9 is the same view as in FIG. 7, with some parts removed better to evidence others;

FIG. 10 is a view from above of FIG. 9;

DETAILED DESCRIPTION

Figure 1:
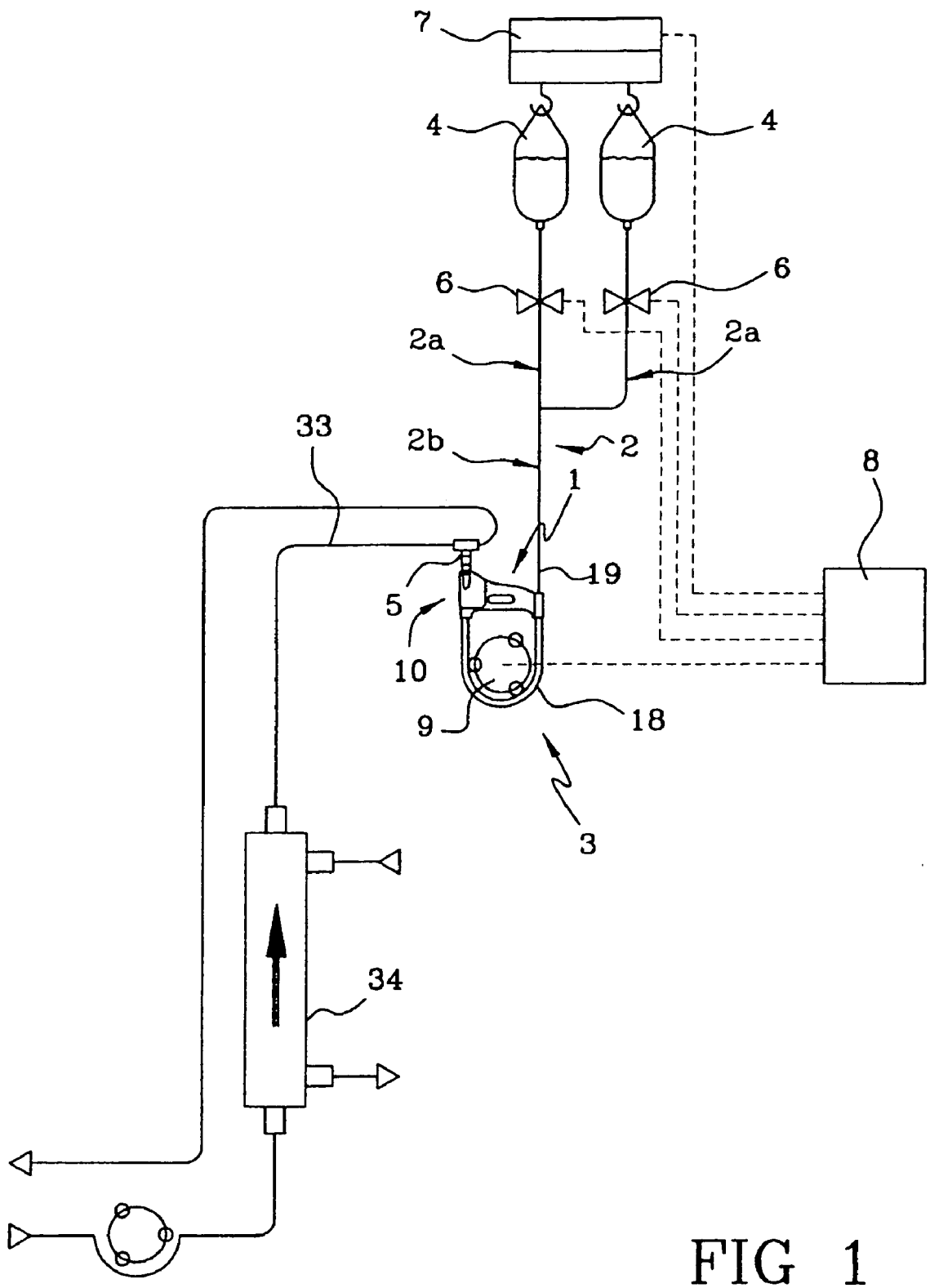
FIG. 1 is a schematic view of an infusion device according to the invention, applied to an extracorporeal blood circuit.
Figure 2:
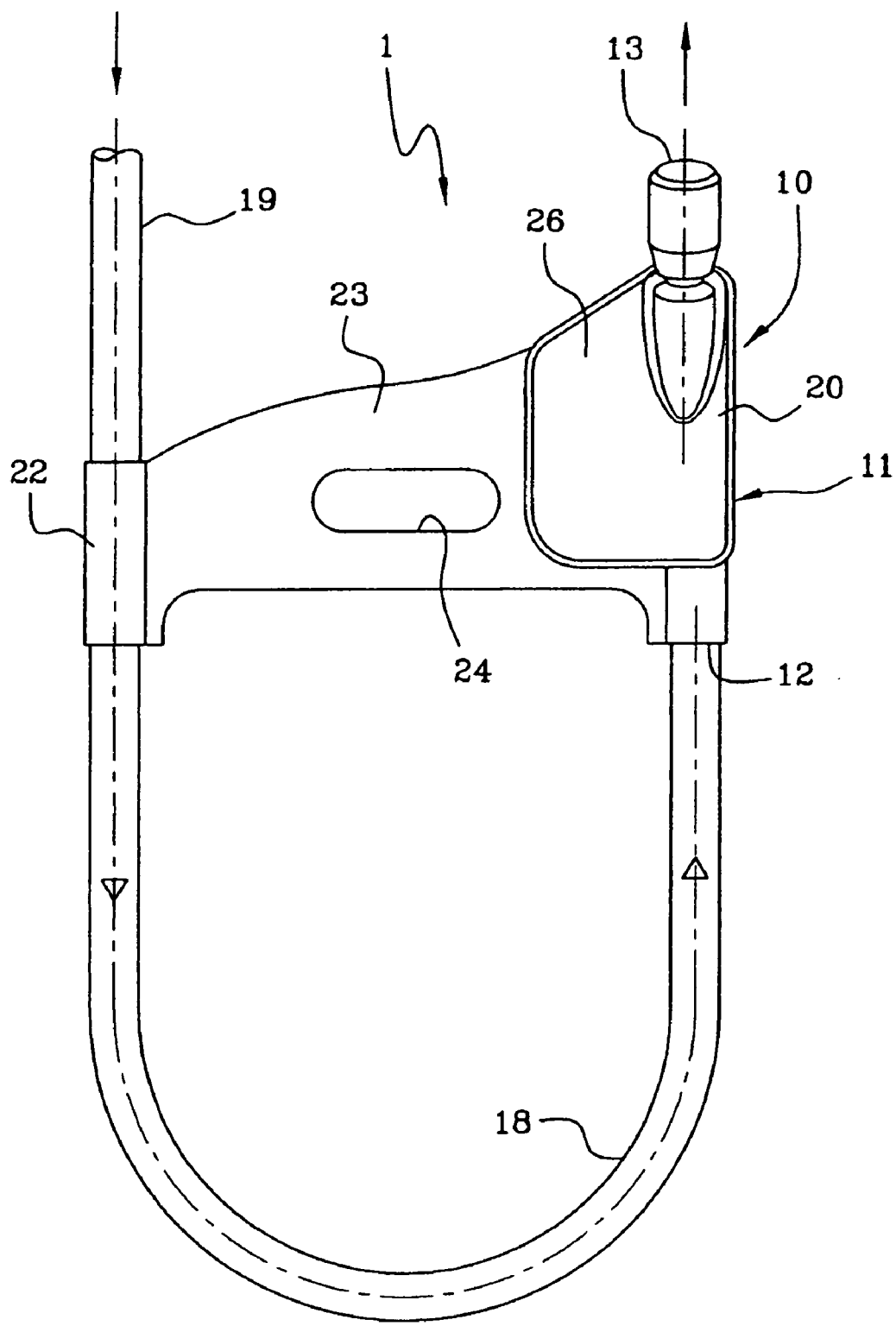
FIG. 2 shows a portion of the device of FIG. 1, comprising a support element and a curved length of tubing.
Figure 3:
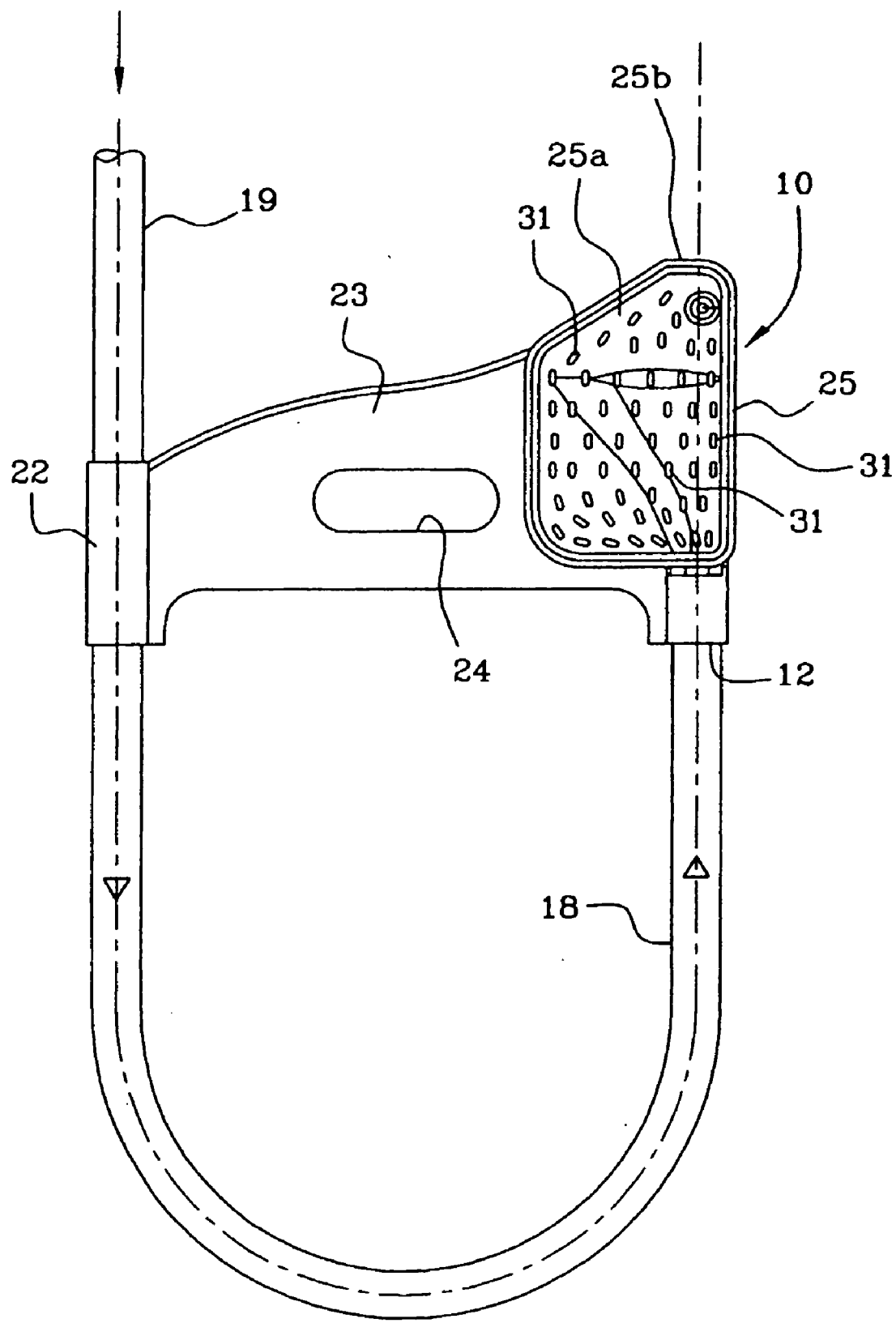
FIG. 3 is a view similar to that of FIG. 2, in which part of the support element has been removed to show its internal structure more clearly.
Figure 6:
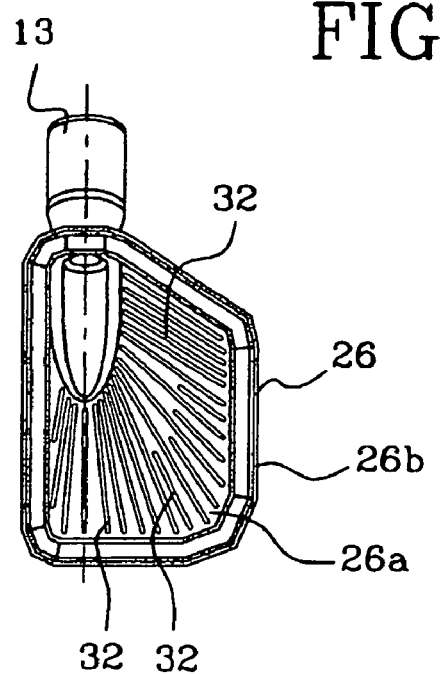
FIG. 6 shows the part of the support element which is removed in the view of FIG. 3.
Figure 4:
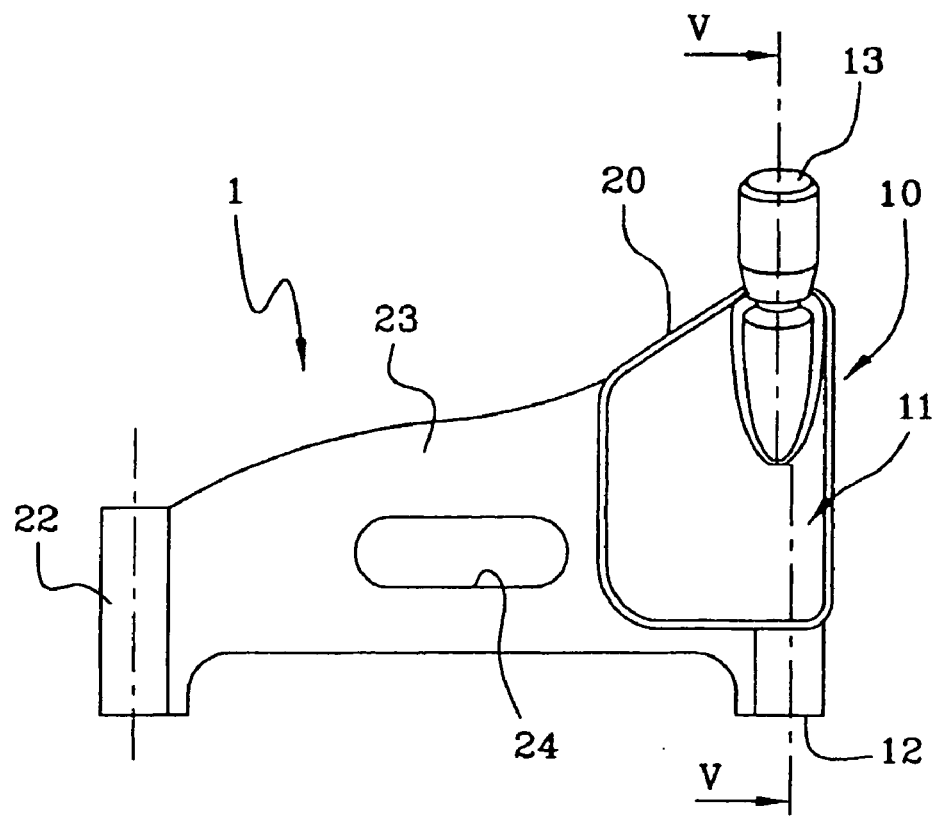
FIG. 4 is a detail view of a support element forming part of the device according to the invention.

With reference to the attached figures, a description will be given of an infusion device 3 according to the invention.

The device 3 has an infusion line 2 and at least one container 4 designed to hold a specified quantity of a liquid to be infused into a patient; in particular, the infusion point 5 can be positioned in a specified area of an extracorporeal blood circuit, or, alternatively, can be connected directly to the patient.

The device 3 can also comprise a plurality of containers 4, which can be sequentially brought into fluid communication with the infusion point by opening and closing corresponding shut-off elements 6, such as clamps or the like, which may be manually or automatically operated.

A weighing device 7, such as a balance, is associated for operation with the infusion liquid container or containers, to detect the total weight of the container or containers and send a corresponding control signal. In practice, the control signal is a signal related to the total weight measured by the balance during the treatment.

This signal is transmitted to a control unit 8 associated with the weighing device; the control unit 8 can sample and store the weight measured by the balance at finite time intervals, for example at regular intervals. Thus the control unit 8 can determine the actual flow passing through the infusion line 2 and suitably adjust movement means associated with the line whenever a discrepancy is found between the actual flow and the desired flow.

It should be noted that the movement means can comprise at least one pump, for example a peristaltic pump 9, or, in the case of gravity operation for example, a flow control valve, for example an electromagnetic clamp.

Typically, the desired flow can be set by the user or pre-programmed in the control unit and, in any case, can be a value which is constant or variable over time. The control unit 8 can determine the decrease in the actual weight of the infusion liquid container, and can adjust the movement means, if necessary, to obtain the desired flow along the line.

When the total weight of the content of each container is known, the control unit 8 can also detect at least a condition of emptying or end of infusion, and activate a corresponding control procedure. This procedure can comprise a stage of commanding the movement means (peristaltic pump 9) to stop the transport of fluid along the line and/or a stage of signalling that the container is empty or that a specified volume of liquid has been used up.

If the infusion device 3 comprises two or more liquid containers 4, the infusion line 2 will also have a plurality of branches 2a, each designed to bring a corresponding container into fluid communication with a common part 2b of the line 2 and thus with the infusion point 5. In this case, each branch 2a has a flow shut-off element 6 which can be switched between an open and a closed position, to selectively permit or prevent the passage of fluid.

The flow shut-off elements 6 can be activated manually or commanded sequentially by the control unit 8. For example, the control unit 8 can be programmed so that, when an empty condition of a container 4 is detected, it can command the closing of the shut-off element 6 located in the branch 2*a* related to the empty container 4, and the opening of one of the shut-off elements 6 located in a branch 2*a* corresponding to a container in which liquid is present. This procedure can be repeated until all the containers have been emptied.

The device in question comprises a continuous fluid separator 10, located in the infusion line 2, for separating the fluid supplied from the container or containers 4 into a gas portion and a liquid portion; this continuous separator 10 can allow only the liquid to continue along the infusion line, while separating and discharging towards the exterior any gas bubbles supplied from the container 4.

In particular, when the infusion liquid in a container 4 has been used up, the separator 10 receives any gas and discharges it to the exterior, thus preventing the passage of gaseous substances downstream of the section in which this separator operates.

The continuous separator 10 comprises a containing body 11 having at least one inlet 12 for receiving a fluid supplied from the container, at least one first outlet 13 for receiving a liquid portion of the flow and sending it downstream of the selector to the infusion point 5, at least one second outlet 14 for receiving the gaseous portion of the fluid and discharging it towards the exterior, and selector means 15 interposed between the inlet 12 and the first outlet 13 and capable of continuously separating the fluid into a gaseous portion and the liquid portion.

The selector means 15 comprise at least one hydrophilic membrane 16 having one side 16*a* facing the first outlet 13 and one side 16*b* facing the inlet 12 for receiving the fluid and transferring only liquid towards the first outlet; the selector means 15 also comprise at least one hydrophobic membrane 17 having one side 17*a* facing the second outlet 14 and one side 17*b* facing the inlet 12 to receive the fluid and transfer only gas towards the second outlet 14.

With reference to the extension of the infusion line, the separator 10 is interposed between the movement means (peristaltic pump 9) and the infusion point 5, and, in particular, is positioned immediately downstream of the movement means.

As can be seen in the attached FIGS. 1 to 6, the device 3 comprises a rigid support element 1, holding opposing portions of a first length of tubing 18 of the line 2 and specifically designed to interact with the movement means (peristaltic pump 9). In practice, the rigid support 1 holds the first length of tubing 18 in such a way that this first length has a curved shape and a specified axial extension.

The support element 1 is positioned transversely with respect to the mid-line axis of the opposing portions of the first length of tubing 18, and enables the line to be manipulated easily to allow the first length 18 to be easily fitted around a rotor of a peristaltic pump 9.

Upstream of this first length of tubing 18, the infusion line comprises a second length of tubing 19 extending between the container 4 and the rigid support 1 and placed in fluid communication with the first length 18. As mentioned, the second length of tubing 19 can consist of a single duct connected to a single liquid container 4, or can branch terminally into a plurality of branches 2*a*, each connected to a corresponding container 4.

A description will now be given of the detailed structure of the rigid support element 1 (FIGS. 1 to 6), which comprises a first lateral portion 20, forming the containing body 11, and a second lateral portion 22, of tubular profile, to which are fixed corresponding ends of the first and the second lengths 18 and 19 of the infusion line 2; the second lateral portion 22 and the first lateral portion 20 are connected rigidly together by a rigid cross-piece 23 provided with at least one through hole 24 which can act as an element for attaching the rigid support 1 to a support wall which is not illustrated; the rigid cross-piece 23 is essentially flat and parallel to a plane in which the first length of tubing 18 lies.

The containing body 11 formed by the first lateral portion 20 comprises a base 25 and a cover portion 26, which interact with each other to form a passage 27 for fluid between the inlet 12, on the one hand, and the first and second outlets 13, 14, on the other hand.

More precisely, the base 25 forms a through channel 28 for putting the passage 27 in fluid communication with the exterior. This through channel 28 extends orthogonally to the plane in which the support element 1 lies, and is located in the proximity of a peripheral area of the base 25; thus, when the infusion device 3 is mounted on the peristaltic pump 9 in operating conditions, the through channel 28 is located in a topmost area of the base 25.

Figure 5:
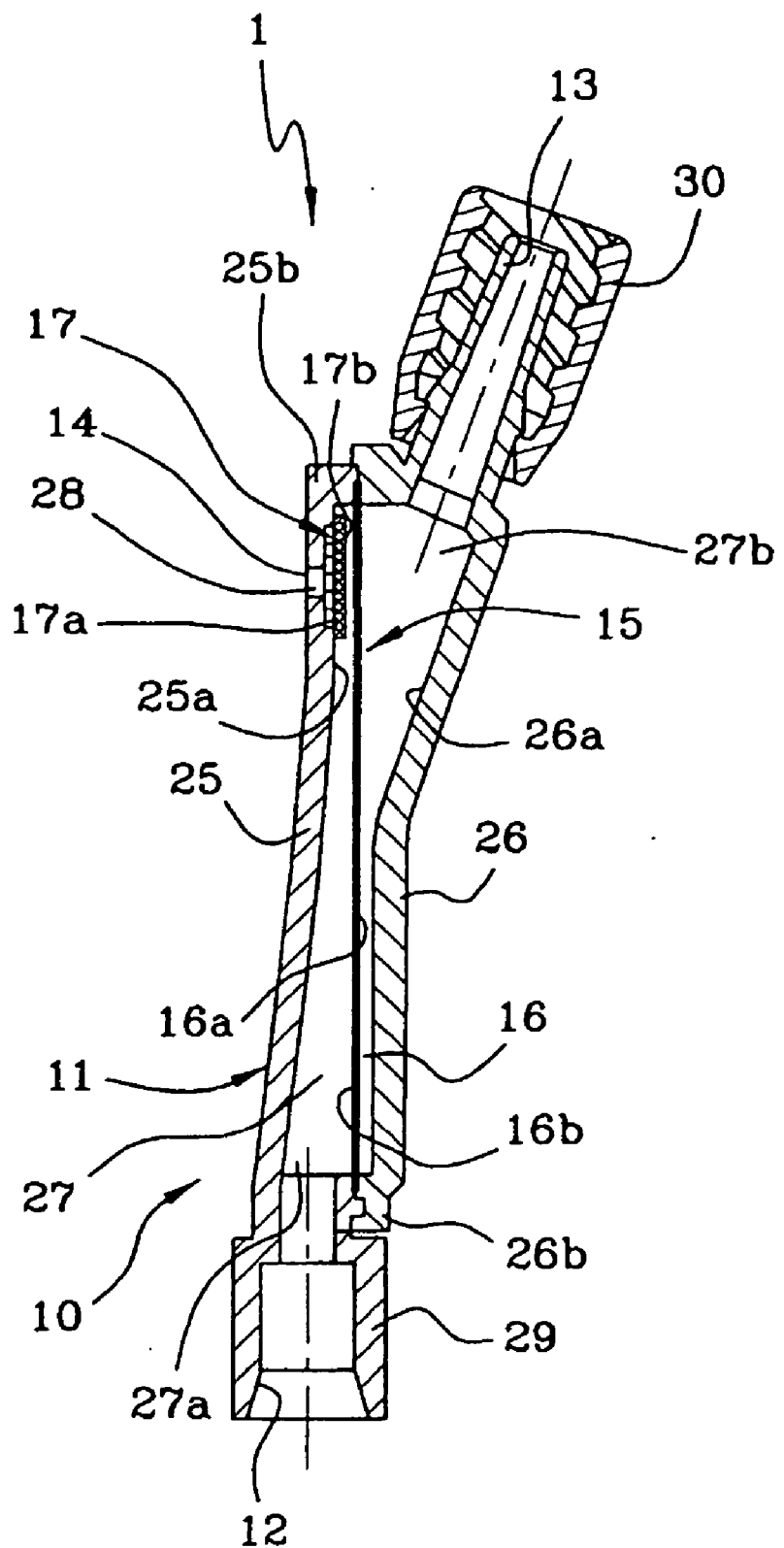
FIG. 5 is a section taken through the line V-V of FIG. 4.
Figure 7:
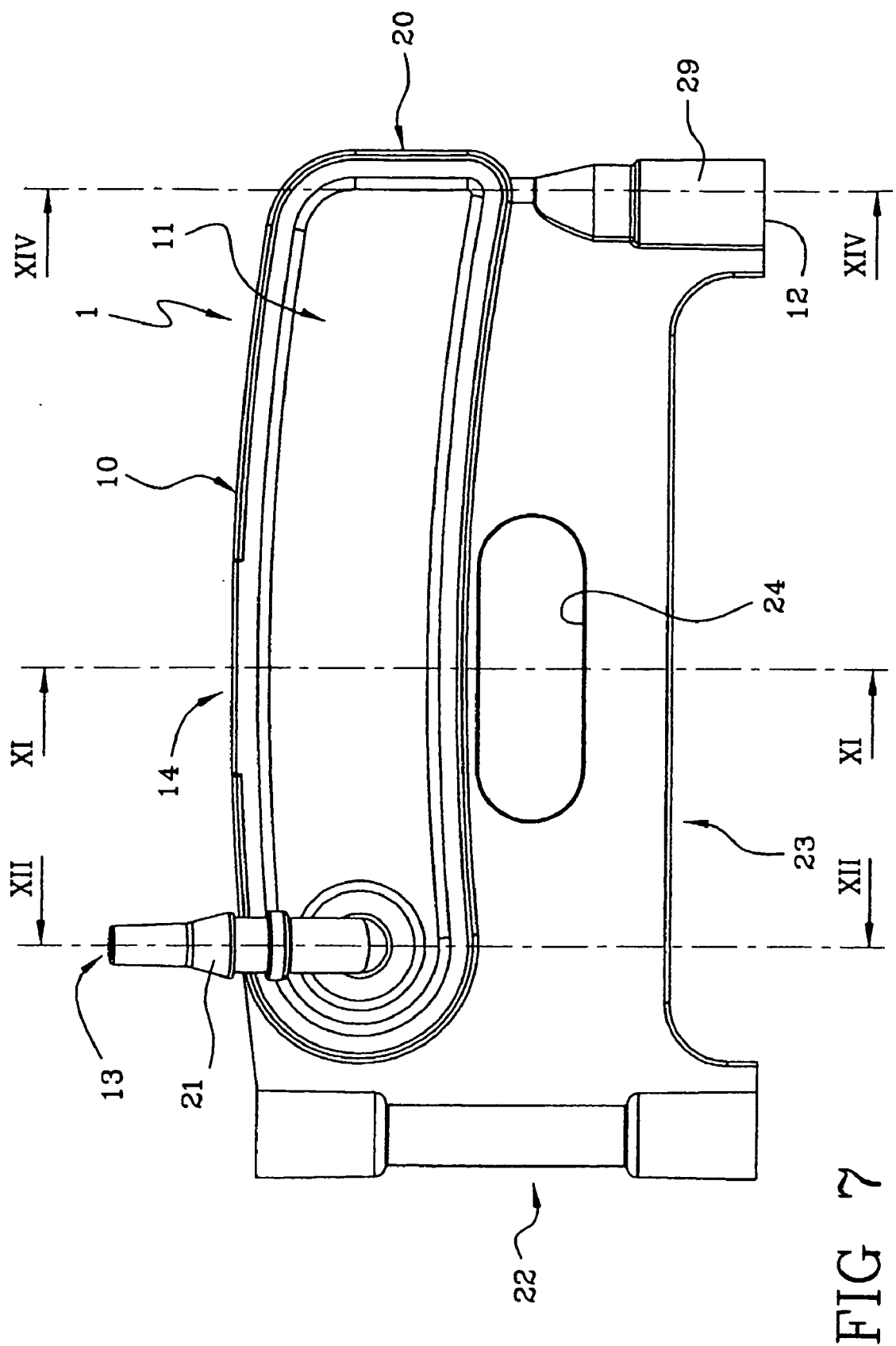
FIG. 7 is a second embodiment of a support element according to the invention, which can be used in substitution for the support element of FIG. 2.
Figure 8:
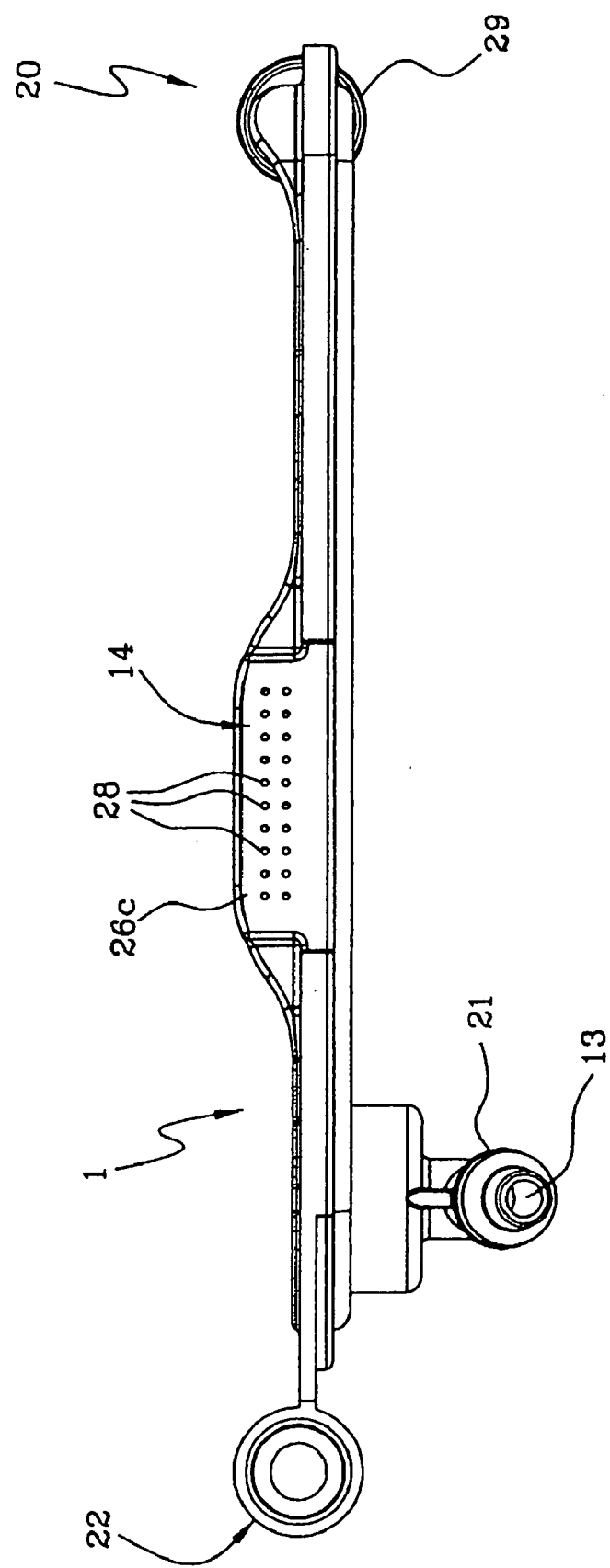
FIG. 8 is a view from above of FIG. 7.
Figure 11:
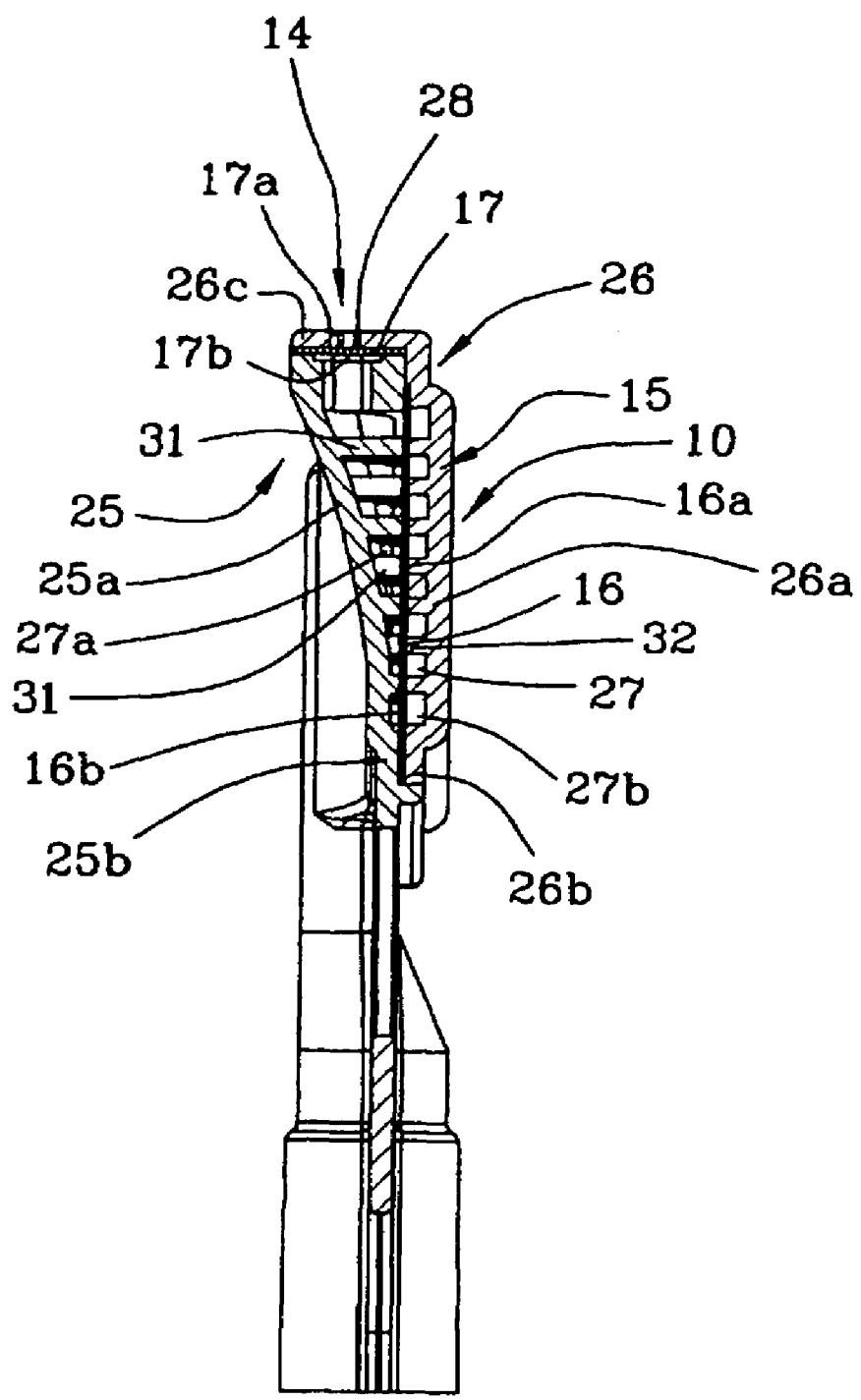
FIG. 11 is a section according to line XI-XI of FIG. 7.
Figure 12:
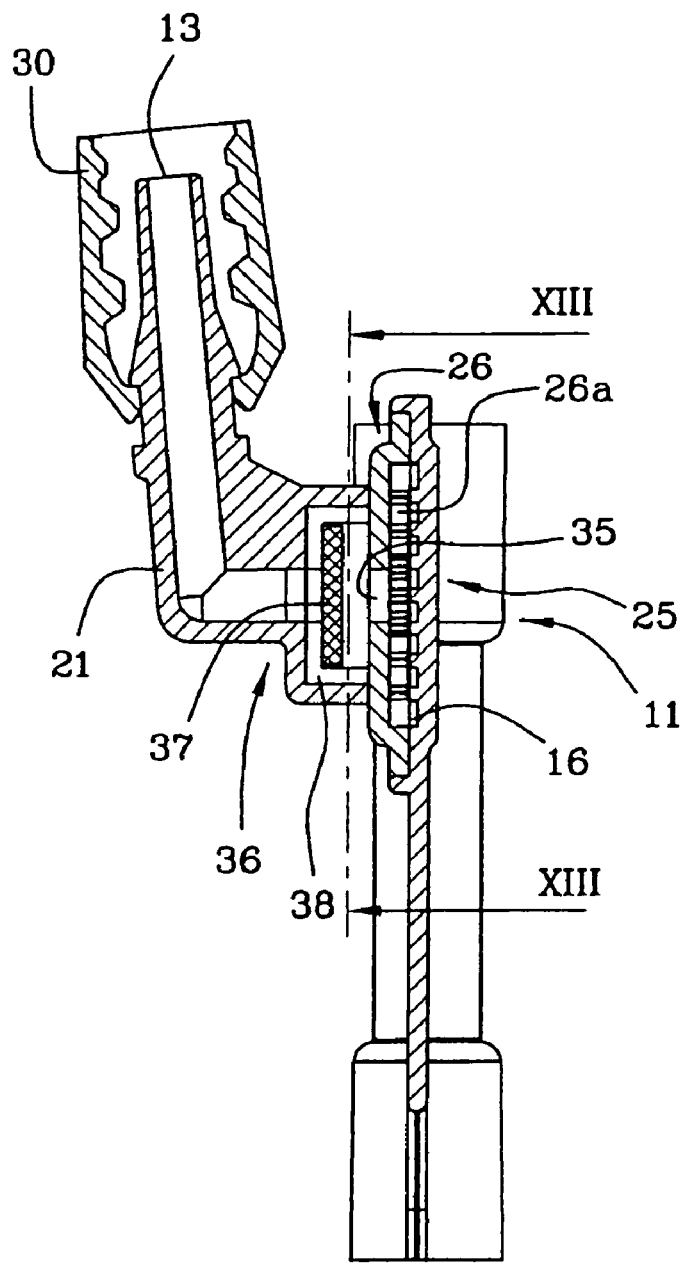
FIG. 12 is a section according to line XII-XII of FIG. 7.
Figure 13:
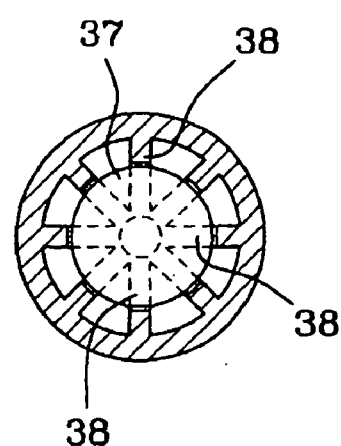
FIG. 13 is a section according to line XIII-XIII of FIG. 12.
Figure 14:
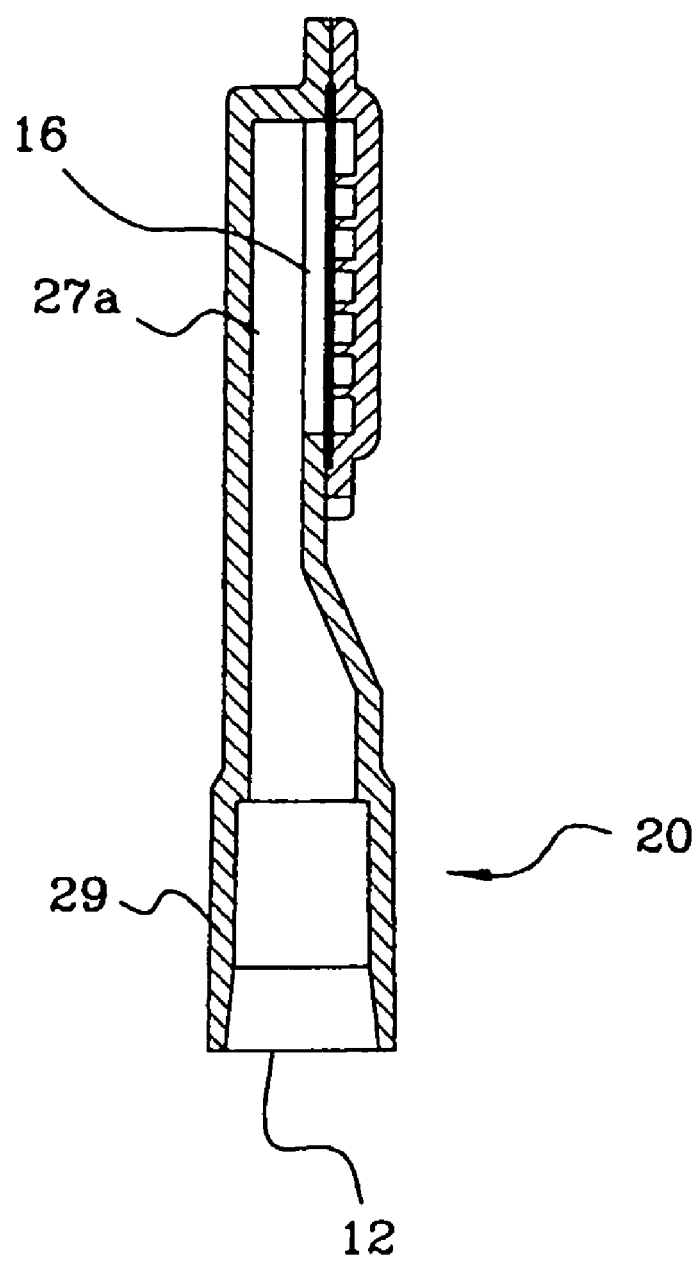
FIG. 14 is a view from inside of a part of the support element which is removed from view in FIG. 9.

As will be seen in FIG. 5, the fluid passage 27 within the containing body 11 is essentially divided by the hydrophilic membrane 16 into two half-parts or chambers 27*a* and 27*b*. Because of its special positioning, the through channel 28 is located in the uppermost point of the chamber 27*a* (located upstream with respect to the direction of flow) into which the passage 27 is divided, in order to discharge any gas efficiently. For this purpose, the hydrophobic membrane 17 operates in an inlet section of the through channel 28 facing the interior of the containing body 11.

With reference to FIG. 5 again, it will be noted that the base 25 comprises an incorporated first tubular connecting element 29 for receiving one end of the first length of tubing 18. In turn, the cover portion 26 comprises an incorporated second tubular connecting element 30 having an axis of extension inclined with respect to that of the first tubular element 29.

The second connecting element 30, for example a Luer connector, can be connected directly to a T-shaped connector of an extracorporeal blood circuit 33, upstream or downstream of a blood treatment unit 34 (a dialysis filter or other device). Thus, since a direct connection to the extracorporeal blood circuit 33 is possible, it becomes unnecessary to have a tube downstream of the separator 10; this provides the advantage of preventing any possible involuntary blockage which would be difficult to detect by means of the sensor system associated with the extracorporeal circuit 33.

It should be noted in this context that any infusion liquid transport tube located downstream of the separator 10 would, if the tube were blocked, cause a pressure stress for a certain period of time, affecting the separator 10 and the membranes 16 and 17 in particular, as well as the liquid seals.

It should also be noted that the rigid support 1 is thin, so that the whole infusion line 2 can occupy very small volumes.

Nevertheless, the efficiency of the system is not reduced, because of the particular structure of the containing body 11 and the positions of the membranes 16 and 17; in particular, the hydrophilic membrane 16 is interposed between the base 25 and the cover portion 26, and extends essentially through the whole containing body 11; the base 25 and the cover portion 26 comprise corresponding base walls 25*a* and 26*a* and corresponding perimeter edges 25*b* and 26*b* emerging from the base walls 25*a* and 26*a* to form the passage through which the fluid is transported.

The hydrophilic membrane 16 extends parallel to the base walls 25*a* and 26*a* in a position spaced from the walls, thus providing an active surface essentially equal to the area of the containing body 11 seen in plan view.

It should also be noted that the containing body 11 has a plurality of projections 31 and 32 emerging from the base wall 25*a* of the base and from the base wall 26*a* of the cover portion.

In detail, the projections 31 associated with the base 25 comprise teeth distributed uniformly over the surface of the base wall 25*a* of the base, while the projections 32 associated with the cover portion 26 comprise angularly spaced deflectors for guiding the liquid flow towards the first outlet 13.

In terms of construction, the base 25 of the containing body, the rigid cross-piece 23 and the second lateral portion 22 are made in a single piece, while the cover portion 26 is fixed to the base 25 after the hydrophobic and hydrophilic membranes 17 and 16 have been placed in position.

Figures from 7 to 14 illustrate a second embodiment of a rigid support element which can be used alternatively to the rigid support element of the first embodiment, described above. In the second embodiment, as in the first, the support element is associable to an infusion device 3, such as the infusion device 3 shown in FIG. 1, and engages opposite portions of the first length of tubing 18 of the infusion line 2, as well as a portion of end of the second length of tubing 19.

For reasons of simplicity and greater clarity, in figures from 7 onwards the support element is denoted by 1, like the support element of the first embodiment, illustrated in figures from 1 to 6. Also, in figures from 7 onwards, the elements in the second embodiment which are similar both structurally and functionally to elements of the first embodiment, are denoted by the same numbers as in figures from 1 to 6.

In the second embodiment, the continuous fluid separator 10 includes a check valve 36 which is predisposed to prevent back-flow in an opposite direction to the flow direction of the extracorporeal fluid.

The check valve 36, or one-way valve, is predisposed along the liquid portion line after the liquid has already been separated from the gas portion by the continuous fluid separator 10. The check valve 36 is arranged internally of the separator containing body 11, in a zone comprised between the separator selector means 15 and the first outlet 13 (liquid outlet).

The check valve 36 comprises a mobile obturator organ 37 operating on a liquid passage mouth 35, through which the liquid portion passes. The obturator organ 37 is disc-shaped and is made of an elastomer material (for example silicone). The obturator organ 37 is mobile inside a chamber which, when the obturator is open, communicates on one side thereof with the fluid passage mouth 35. In the presence of a flow in the opposite direction to the desired direction, i.e. from the infusion point towards the separator 10, the obturator organ 37 automatically shuts the liquid passage mouth 35, interrupting the back-flow, so that the fluid in the extracorporeal circuit 33 cannot reach the separator 10.

The chamber housing the obturator organ 37 also communicates, with no possibility of shutting-off by the obturator, with the separator first outlet 13, on the opposite side to the liquid passage mouth 35. The check valve 36 is provided with means for preventing the obturator 37 from closing communication with the first outlet 13. The means for preventing are in the present embodiment constituted by at least one projection 38 which emerges from at least one wall delimiting the chamber containing the obturator 37, which projection 38 can interact contactingly with the obturator 37. In the illustrated embodiment a plurality of projections 38 are present, arranged in spoke fashion, each L-shaped and cooperating to contain the obturator 37 laterally.

The liquid passage mouth 35 is associated to the cover portion 26 of the containing body 11. In particular, the passage mouth 35 is arranged on the base wall 26*a* of the cover portion 26, which the hydrophilic membrane 16 faces at a distanced position therefrom.

As in the first embodiment, the containing body 11 internally affords a fluid passage 27 between the inlet 12 and the first outlet 13. This fluid passage 27 has an upstream portion 27*a*, comprised between the inlet 12 and the hydrophilic membrane 16, and a downstream portion 27*b*, comprised between the hydrophilic membrane 16 and the first outlet 13. The base wall 26*a*, on which the passage mouth 35 is afforded, delimits the downstream portion 27*b* of the fluid passage.

The passage mouth 35 is situated in a lateral end zone of the base wall 26*a* (see FIG. 15), which lateral end zone is opposite to the lateral end position in which the fluid inlet 12 is situated in the containing body 11.

Figure 15:
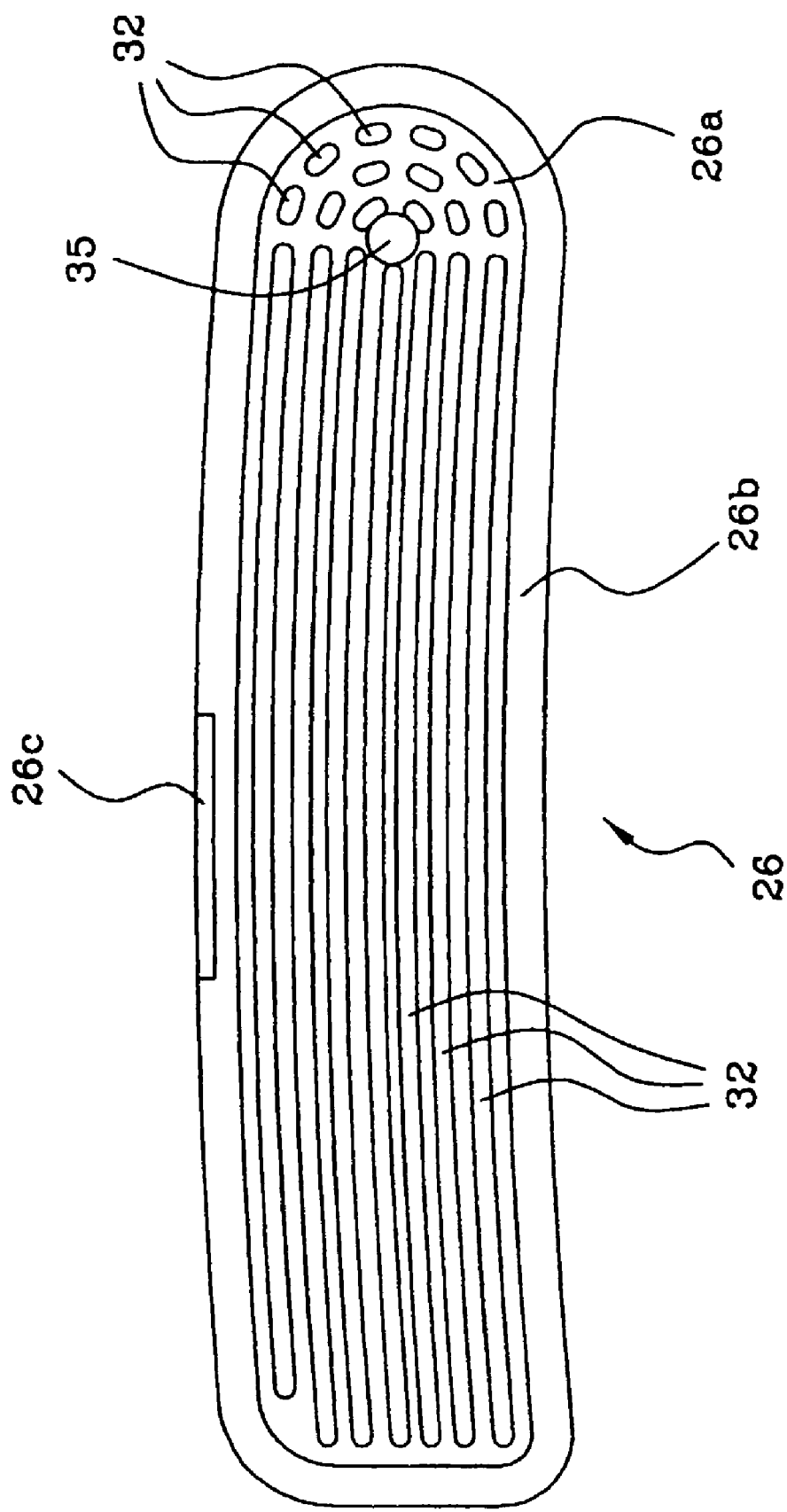
FIG. 15 is a view of a cover portion of a containing body according to the invention.

As illustrated in FIG. 15, the projections 32, arranged on the internal side of the base wall 26*a*, are subdivided into a first group of projections, which reach as far as the passage mouth 35, where the projections 32 are conformed in lines, parallel to one another and extending in a horizontal direction towards the passage mouth 35, defining a plurality of parallel linear conduits oriented in the direction of the liquid portion pathway; and into a second group of projections, arranged beyond the passage mouth 35, in which the projections 32 are like teeth, serrated and shaped as points or small segments, and are oriented tangentially with respect to the centre of the passage mouth 35.

The first outlet 13 is arranged at an upper end of an L-shaped outlet conduit 21. The upper end has an inclined axis with respect to the lie plane of the support element 1. The outlet conduit 21 is solidly associated to the cover portion 26 of the containing body.

The hydrophobic membrane 17, which operates on the second outlet 14 (vent) is situated in an upper zone of the upstream portion 27*a* of the fluid passage, where the term upper is used in reference to a use configuration in which the lie plane of the first U-shaped length of tubing 18 is vertical. In the use configuration the hydrophobic membrane 17 is situated at the highest point of the upstream portion 27*a*, and faces upwards.

In the use configuration, the hydrophobic membrane 17 has a horizontal lie plane, while the hydrophilic membrane 16 has a vertical lie plane. The hydrophobic membrane 17 is situated above the highest point of the operative filtering surface of the hydrophilic membrane 16. The hydrophilic membrane operative filtering surface does not comprise the perimeter edge of the hydrophilic membrane 16, which is constrained between the perimeter edges of the base 25*b* and the cover portion perimeter edges 26*b*.

The upstream portion 27*a* of the fluid passage has a flat conformation, with one dimension being smaller than the other two, with a lie plane that is parallel to the hydrophilic membrane 16, and thus vertical in the in-use configuration. The upstream portion 27*a* of the fluid passage has a fluid inlet which is arranged in a lower end zone of the upstream portion 27a itself, on an opposite side to the upper second outlet 14 for gas, where the hydrophobic membrane 17 is operative.

The passage section of the upstream portion 27a of the fluid passage increases gradually going from bottom to top, in the direction of the hydrophobic membrane 17, and then towards the second outlet 14. An upper end zone of the upstream portion 27a, superiorly delimited by the hydrophobic membrane 17, is located above the upper edge of the hydrophilic membrane operative filtering surface.

In the second embodiment, the through channel 28, which places the upstream portion 27a of the fluid passage 27 in communication with the outside atmosphere, through the hydrophobic membrane 17, has a longitudinal axis which extends parallel to the lie plane of the support element 1, and is afforded in a wing 26c of the cover portion 26. The wing 26c projects from an upper end of the cover portion 26, in a transversal direction to the direction of the lie plane of the main body of the cover portion 26.

The through channel 28 can be made, as in the illustrated embodiment, in the form of a plurality of uniformly-distributed vertical-axis holes.

The hydrophobic membrane 17 is kept in position thanks to a perimeter edge, constrained between an upper mouth of the base 25 and the wing 26c of the cover portion 26.

The base wall 25a of the base, which delimits the upstream portions 27a, has an inclined central part which is arranged at the vertical of the second outlet 14. Thanks to this inclination, the upstream portion 27a of the fluid passage has a central zone, arranged below the vertical of the second outlet 14, having a passage section which increases going from the bottom towards the top thereof. The height of the projections 31 (cooperating with the projections 32 to prevent excessive deformation of the filtering hydrophilic membrane 16) also increases in an upwards direction in this central zone.

In this central zone, the projections 31 are tooth-shaped, and are staggered among themselves with in a horizontal direction. The teeth, for example, can be pointed, aligned in vertical rows, or can be in short segments arranged vertically according to a plan view (FIG. 9); in a lateral end zone, close to the separator fluid inlet 12, the projections 31 are horizontally-arranged lines (on the right in FIG. 9); in another lateral end zone, opposite the fluid inlet, the projections 31 are C-shaped, arranged concentrically one inside another and with the arms of the C-shape elongate in a horizontal direction (on the left in FIG. 9).

The linear projections 31 define linear conduits, which direct the fluid towards the central zone of the upstream portion 27a, lying below the second outlet 14. The C-shaped projections 31 define C-shaped conduits which lead the fluid towards the central zone.

The projections 31 and 32 define two rest planes for both opposite sides 16b and 16a of the hydrophilic membrane, enabling deformations of the membrane in both directions to be limited.

The special arrangement and conformation of the upstream portion 27a, as well as the special arrangement and conformation of the second outlet 14 and the fluid inlet 12, contribute to improving the efficiency of the gas elimination from the fluid, while occupying only a relatively compact space.

In the second embodiment, the containing body 11 is incorporated in the support element 1 and develops prevalently in a transversal direction, from the first lateral portion 20 to the second lateral portion 22. The fluid inlet 12 is situated in the first lateral portion 20, while the first outlet 13, for liquid only, is located in a lateral end zone of the above-mentioned transversal development, beyond the median line of the development and in proximity of the second lateral portion 22. This enables the hydrophilic membrane 16 to have a large active filtration surface, and exploits to the full the space on the rigid cross-piece 23 without increasing the overall mass of the support element 1.

The second outlet 14, for gas (vent), is arranged in an intermediate zone of the transversal development of the containing body 11.

The check valve 36 predisposition prevents back-flow: in particular, the check valve 36 is a guarantee against any risk of passage of blood from the extracorporeal circuit 33 to the infusion line 2. The risk is particularly high in a case where the peristaltic pump 9, for any reason, loses its occluding capacity, i.e. the function of shutting off the first length of tubing 18, by effect of the squeezing of the flexible walls of the tubes in the contact zone between the tubes and the pump rollers. In the absence of this occluding function, blood might flow from the extracorporeal circuit 33, through the infusion line and even up to the containers 4, seriously injuring the patient.

Furthermore, using the check valve 36 prevents inlet of small quantities of blood coming from the extracorporeal circuit 33 into the infusion line 2, in particular the zone thereof comprised between the peristaltic pump 9 and the infusion point 5. This situation might occur due to the operating mode of the peristaltic pump 9, which causes an inconstant pressure in the infusion line 2, with the risk of possible blood leaks during the phase of operation in which the pressure drops.

The continuous fluid separator 10 of air and liquid, which has been described in two possible embodiments, is incorporated into a support element 1, predisposed to support a first length of tubing 18, in fluid connection with a second length of tubing 19, also constrained to the support element 1, included in an infusion line 2 which is part of an infusion device 3.

In a further embodiment, not illustrated, of an infusion device according to the present invention, the check valve 36 can be not incorporated with the air-liquid separator, but can instead be included in the infusion line, located at a distance after the separator.

Also possible is the use of a gas-liquid separator, structured as the ones described herein above, not necessarily incorporated in the support element 1 but independent thereof, and inserted in a fluid transport line, which can be different from the one described herein above, for de-aerating the fluid conveyed.

| Legend: | |
| --- | --- |
| 1 | support element |
| 2 | infusion line |
| 2a | branches of infusion line |
| 2b | common part of infusion line |
| 3 | infusion device |
| 4 | containers |
| 5 | infusion point |
| 6 | flow shut-off elements |
| 7 | weighing device |
| 8 | control unit |
| 9 | peristaltic pump |
| 10 | continuous fluid separator (or deaerator device) |
| 11 | separator containing body |
| 12 | separator inlet (fluid inlet) |

-continued

Legend:

| | |
|---|---|
| 13 | separator first outlet (liquid outlet) |
| 14 | separator second outlet (gas outlet) |
| 15 | separator selector means |
| 16 | hydrophilic membrane (liquid portion passage) |
| 16a | hydrophilic membrane side facing liquid outlet |
| 16b | hydrophilic membrane side facing fluid inlet |
| 17 | hydrophobic membrane (gas portion passage) |
| 17a | hydrophobic membrane side facing gas outlet |
| 17b | hydrophobic membrane side facing fluid inlet |
| 18 | first length of tubing (pump segment) |
| 19 | second length of tubing |
| 20 | first lateral portion of support element |
| 21 | outlet conduit |
| 22 | second lateral portion of support element |
| 23 | rigid cross-piece of support element |
| 24 | through hole of support element |
| 25 | base of containing body |
| 25a | base wall of base |
| 25b | perimeter edge of base |
| 26 | cover portion of containing body |
| 26a | base wall of cover portion |
| 26b | perimeter edge of cover portion |
| 26c | upper transversal wing |
| 27 | fluid passage within containing body |
| 27a | fluid passage half-part upstream hydrophilic membrane |
| 27b | fluid passage half-part downstream hydrophilic membrane |
| 28 | through channel within containing body |
| 29 | first tubular connecting element |
| 30 | second tubular connecting element |
| 31 | projections associated to containing body base |
| 32 | projections associated to containing body cover portion |
| 33 | extracorporeal blood circuit |
| 34 | blood treatment unit |
| 35 | liquid passage mouth |
| 36 | check valve |
| 37 | mobile obturator organ |
| 38 | check valve projections |

The invention claimed is:

1. An infusion device for medical use, comprising:
at least one container designed to hold a specified quantity of a liquid to be infused into a patient;
a weighing device associated for operation with said container to measure the weight of the container and emit a corresponding control signal;
a transport line connected to said container to convey the liquid, in operating conditions, towards an infusion point;
means for moving a flow of the liquid along said line;
a rigid support holding opposite ends of a first length of tubing of said line designed to interact with said movement means, said first length of tubing having a curved shape and a predetermined axial extension;
a control unit associated with said weighing device and with said movement means, the control unit receiving said control signal and being capable of detecting at least one end of infusion condition, said control unit being configured to perform an appropriate end of infusion procedure when an end of infusion condition is detected;
a continuous fluid separator capable of separating the fluid into a gaseous portion and a liquid portion, said separator operating in said transport line between said movement means and said infusion point, said separator comprising a containing body, said rigid support comprising a first portion forming said containing body, said containing body having:
at least one inlet for receiving a fluid from said container;
at least a first outlet for receiving a liquid portion of said fluid, said containing body internally defining a fluid passage between said inlet and said first outlet;
at least a second outlet for receiving a gaseous portion of said fluid; and
selector means interposed between said inlet and said first outlet and capable of continuously separating said fluid into a gaseous portion and a liquid portion, said selector means comprising at least one hydrophilic membrane having one side facing said first outlet and one side facing said inlet, for receiving said fluid and transferring only liquid towards said first outlet, said selector means further comprising at least one hydrophobic membrane having one side facing said second outlet and one side facing said inlet, for receiving said fluid and transferring only gas towards said second outlet, said hydrophobic membrane being situated, in a use configuration of said first length of tubing, in an upper zone of an upstream portion of said fluid passage, said upstream portion being located upstream of said hydrophilic membrane;
at least one check valve predisposed on said transport line to prevent a flow which is inverse to an infusion direction, said check valve being arranged internally of said containing body in a zone comprised between said selector means and said first outlet.

2. The device of claim 1, wherein said separator is positioned immediately downstream of said movement means.

3. The device of claim 1, wherein said line comprises a second length of tubing extending between said container and said rigid support and put into fluid communication with said first length.

4. The device of claim 1, wherein said rigid support comprises a second lateral portion with a tubular profile to which are fixed corresponding ends of said first and said second length of tubing of said line, said second lateral portion being distanced from said first portion.

5. The device of claim 4, wherein said first and second lateral portions are rigidly connected by a rigid cross-piece.

6. The device of claim 5, wherein said base of said containing body, said rigid cross-piece and said second lateral portion are made in a single piece.

7. The device of claim 5, wherein said rigid cross-piece is essentially flat and parallel to a lie plane of said first length of tubing.

8. The device of claim 4, wherein said containing body has a development which is prevalently in a transversal direction proceeding from said first portion to said second portion, said first outlet being located in a lateral end zone of said transversal development, in proximity of said second portion.

9. The device of claim 8, wherein said second outlet is arranged in an intermediate zone of said transversal development.

10. The device of claim 1, wherein said containing body comprises a base and a cover portion, interacting with each other to form a passage for fluid between said inlet and said first and second outlets.

11. The device of claim 10, wherein said base forms a through channel for putting said passage into fluid communication with the exterior, a hydrophobic membrane operating in said channel.

12. The device of claim 10, wherein said base comprises an incorporated first tubular connecting element.

13. The device of claim 12, wherein said cover portion comprises an incorporated second tubular connecting element having an axis of extension which is inclined with respect to an axis of extension of said first tubular connecting element.

14. The device of claim 10, wherein said hydrophilic membrane is interpositioned between said base and said cover portion, and extends throughout said containing body.

15. The device of claim 10, wherein each of said base and said cover portion comprises a corresponding base wall and a corresponding perimeter edge emerging from said base wall, a hydrophilic membrane extending parallel to said base wall and distanced there-from.

16. The device of claim 15, wherein said containing body has a plurality of projections emerging from said base wall of said base.

17. The device of claim 16, wherein said base projections comprise teeth distributed uniformly over the surface of said base wall of said base.

18. The device of claim 15, wherein said containing body has a plurality of projections emerging from said base wall of said cover portion.

19. The device of claim 18, wherein said cover portion projections comprise deflectors spaced angularly to guide a flow of liquid towards said first outlet.

20. The device of claim 1, wherein said end of infusion procedure comprises a stage of commanding said movement means to stop transport of said fluid along said line.

21. The device of claim 1, wherein said end of infusion procedure comprises a stage of signalling that the end of infusion condition has been reached.

22. The device of claim 1, comprising a plurality of said containers, said transport line exhibiting a plurality of branches for fluid connection of each container to said infusion point, and a corresponding flow shut-off element acting on each of said branches.

23. The device of claim 22, wherein said control unit is capable of performing an appropriate end of infusion procedure when the end of infusion condition is detected, said end of infusion procedure comprising a stage of commanding an opening of a shut-off element associated with a container which is not empty.

24. The device of claim 1, wherein said check valve is an integral part of said rigid support.

25. The device of claim 1, wherein said check valve comprises a mobile obturator organ, which operates on a passage mouth of said liquid portion.

26. The device of claim 25, wherein said passage mouth is associated with a cover portion of said containing body.

27. The device of claim 26, wherein said cover portion comprises a base wall and wherein said selector means comprises at least one hydrophilic membrane facing and distanced from said base wall, said passage mouth being associated to said base wall.

28. The device of claim 1, wherein said hydrophobic membrane faces upwards in a use configuration of said support element.

29. The device of claim 1, wherein said upstream passage portion for fluid passage has at least one passage section which progressively increases in a direction towards said hydrophobic membrane.

30. The device of claim 1, wherein said hydrophobic membrane is located superiorly with respect to an upper point of the operative surface of said hydrophilic membrane.

31. An apparatus for extracorporeal blood treatment comprising an extracorporeal blood circuit, a blood treatment unit positioned in said extracorporeal blood circuit, and a device according to claim 1, said device being connected to a connector of said extracorporeal blood circuit upstream or downstream of said blood treatment unit.

* * * * *